(12) United States Patent
Yamashita et al.

(10) Patent No.: US 7,709,773 B2
(45) Date of Patent: May 4, 2010

(54) SCANNING OPTICAL DEVICE WHICH SETS HARDWARE IN ASSOCIATION WITH A DEPTH OF A FOCUS POSITION BASED ON HARDWARE SET VALUES STORED IN ASSOCIATION WITH DEPTHS OF FOCUS POSITIONS

(75) Inventors: Yusuke Yamashita, Hachioji (JP); Junichi Okada, Hachioji (JP); Makio Ueno, Nagano (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/060,432

(22) Filed: Apr. 1, 2008

(65) Prior Publication Data

US 2008/0251689 A1    Oct. 16, 2008

(30) Foreign Application Priority Data

Apr. 13, 2007  (JP) .............................. 2007-105568

(51) Int. Cl.
*G02B 7/04* (2006.01)
*G02B 27/40* (2006.01)
*G02B 27/64* (2006.01)

(52) U.S. Cl. .................. 250/201.3; 250/458.1; 359/368

(58) Field of Classification Search ............... 250/201.3, 250/208.1, 216, 458.1, 459.1; 359/385, 368
See application file for complete search history.

(56) References Cited

U.S. PATENT DOCUMENTS 6,072,561 A * 6/2000 Sakakibara .................. 355/53

2004/0233944 A1 * 11/2004 Dantus et al. .................. 372/25
2005/0046936 A1 * 3/2005 Dixon et al. ................. 359/385

FOREIGN PATENT DOCUMENTS

JP         2000-275541 A    10/2000

OTHER PUBLICATIONS

Vincent Daria, Caesar Saloma, Osamu Nakamura and Satoshi Kawata, article entitled Contrast Compensation in Two-Photon Fluorescence Imaging Through a Scattering Medium, Proceedings 20th meeting of Japan Society, Laser Microscopy, (SLM-20), pp. 7-12, Tokyo, 1997.

* cited by examiner

*Primary Examiner*—Georgia Y Epps
*Assistant Examiner*—Francis M Legasse, Jr.
(74) *Attorney, Agent, or Firm*—Frishauf, Holtz, Goodman & Chick, P.C.

(57) ABSTRACT

A clear fluorescence image is easily obtained irrespective of variation of scattering due to variation of the depth of a focus position in a specimen. A scanning optical device includes a laser light source for emitting laser light, a scanning unit for scanning the laser light emitted from the laser light source on the specimen, a focus depth adjusting unit for adjusting the depth of the focus position in the specimen of the laser light to be scanned, a fluorescence detector for detecting fluorescence generated from the focus position of the laser light in the specimen, a reference depth information storage unit for storing the absolute height of a predetermined reference depth of the focus position of the laser light in the specimen by the focus depth adjusting unit, and a hardware setting storage unit for storing the relative height to the absolute height of the reference depth at each focus position of the laser light and at least one set value of the laser light source, the scanning unit, and the fluorescence detector in association with each other.

11 Claims, 10 Drawing Sheets

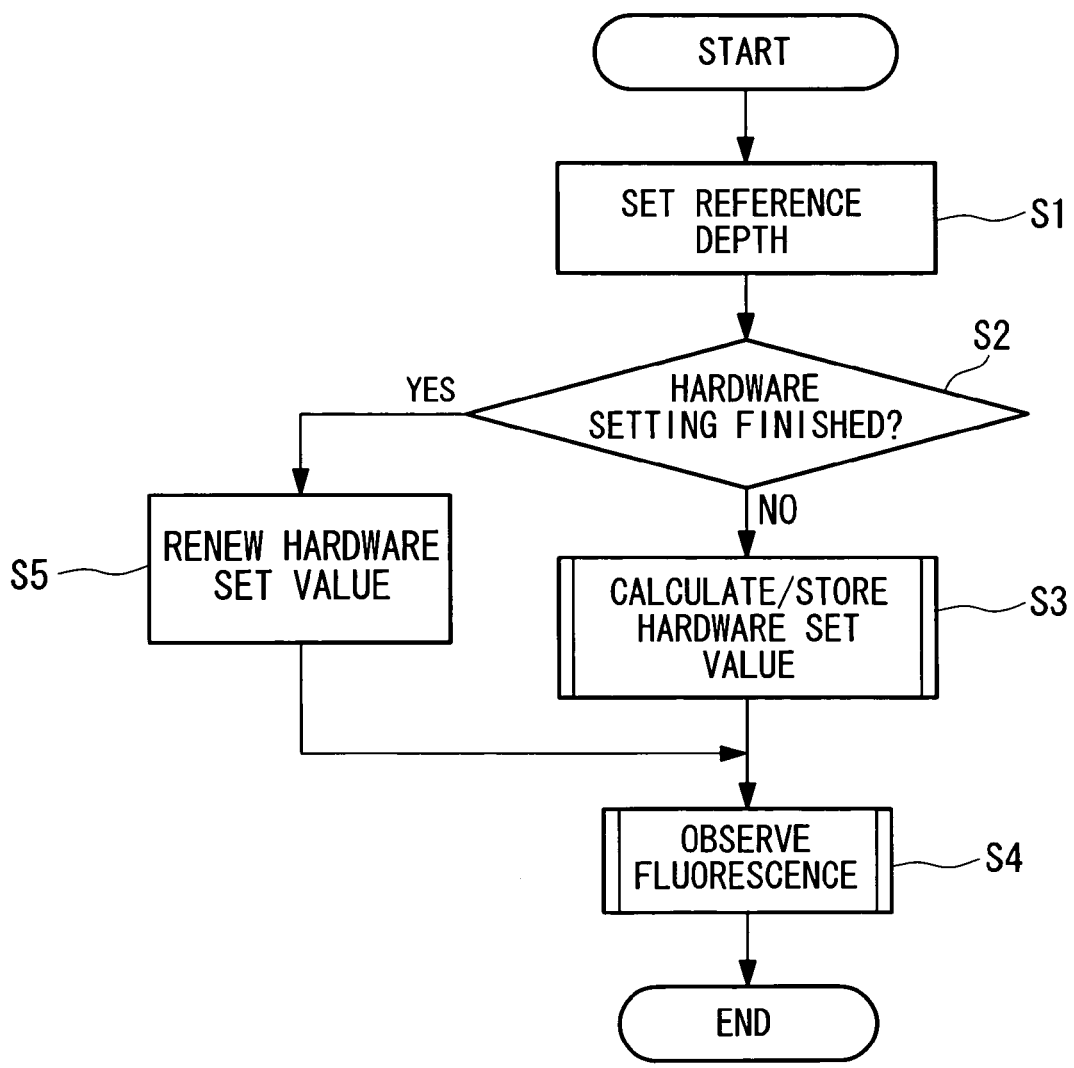

SCANNING OPTICAL DEVICE WHICH SETS HARDWARE IN ASSOCIATION WITH A DEPTH OF A FOCUS POSITION BASED ON HARDWARE SET VALUES STORED IN ASSOCIATION WITH DEPTHS OF FOCUS POSITIONS

BACKGROUND OF THE INVENTION

1. Field of the Invention

The present invention relates to a scanning optical device and an observation method.

This application is based on Japanese Patent Application No. 2007-105568, the content of which is incorporated herein by reference.

2. Description of Related Art

There has been hitherto known a scanning optical device for obtaining a bright fluorescence image having high resolution in the depth direction of a specimen by using a multiphoton excitation phenomenon. Fluorescence emitted from the inside of the specimen is scattered by the specimen, and thus there is a problem that a fluorescence image based on fluorescence generated at a deep position of the specimen is darker than a fluorescence image based on fluorescence generated at a shallow position of the specimen.

In order to solve this problem, for example, according to the invention disclosed in Japanese Unexamined Patent Application, Publication No. 2000-275541, obtained image data are subjected to image processing to correct apparent variation in brightness on a screen.

However, when the correction is made by subjecting obtained image data to the image processing, it induces a problem that the amount of brightness information contained in the image data itself is reduced and thus the corrected fluorescence image is unclear. For example, when a light source, an optical scanning portion, or a photodetector is adjusted so that a fluorescence image based on fluorescence generated at a shallow position of a specimen is clear, a fluorescence image obtained by detecting fluorescence generated at a deep position of the specimen is dark as a whole and has a small amount of brightness information. Therefore, even when the brightness is corrected by the image processing, no clear image can be constructed.

Conversely, when the light source, the optical scanning portion or the photodetector is adjusted so that a fluorescence image based on fluorescence generated at a deep position of the specimen is clear, a fluorescence image obtained by detecting fluorescence generated at a shallow position of the specimen is saturated in brightness, and thus even when the brightness is corrected by the image processing, no clear image can be constructed likewise.

That is, in order to obtain a clear fluorescence image irrespective of the depth of the specimen, it is necessary to obtain a fluorescence image having the same brightness without conducting the image processing.

Furthermore, when an observation position is moved in a horizontal direction with respect to a specimen having an undulating surface, the depth of a focus position in the specimen varies in spite of no variation in the absolute height of the focus position of exciting light at the device side, so that the magnitude of scattering varies.

BRIEF SUMMARY OF THE INVENTION

The present invention provides a scanning optical device and an observation method that can easily obtain a clear fluorescence image irrespective of variation of scattering due to variation in depth of the focus position in a specimen.

A first aspect of the present invention is a scanning optical device including a laser light source for emitting laser light, a scanning unit for scanning the surface of a specimen with the laser light emitted from the laser light source, a focus depth adjusting unit for adjusting the depth of a focus position in the specimen of the laser light scanned by the scanning unit, a fluorescence detector for detecting fluorescence generated from the focus position of the laser light in the specimen, an reference depth information storage unit for storing an absolute height of a predetermined reference depth of the focus position adjusted by the focus depth adjusting unit, and a hardware setting storage unit for storing a relative height to the absolute height of the reference depth at each focus position of the laser light and a hardware set value containing a set value of at least one of the laser light source, the scanning unit, and the fluorescence detector in association with each other.

According to the first aspect of the present invention, the laser light emitted from the laser light source is scanned on the specimen by operating the scanning unit, and focused to the depth position in the specimen which is adjusted by operating the focusing depth adjusting unit, whereby fluorescence is generated in the specimen. The fluorescence generated in the specimen is detected by the fluorescence detector. A fluorescence image can be obtained on the basis of the scanning position of the scanning unit and the intensity information of the fluorescence detected by the fluorescence detector.

In this case, when fluorescence images are obtained while varying the depth of the focus position of the laser light at the same scanning position, the focus depth adjusting unit is operated on the basis of the absolute height of the predetermined reference position of the laser light stored in the reference depth information storage unit and the relative height to the absolute height of the reference depth at each focus position which is stored in the hardware setting storage unit, and hardware such as the laser light source, the scanning unit or the fluorescence detector can be set, on a focus-position basis, in the hardware set value which is stored in association with the relative height in the hardware setting storage unit.

As a result, the setting of the hardware can be implemented every focus position in consideration of the effects such as scattering, etc. caused by the thickness of the specimen, whereby proper fluorescence observation can be performed at all the focus positions. The predetermined reference depth is set to the surface position of the specimen, for example. When the relative height stored in the hardware setting storage unit is not continuous, stored plural relative heights and hardware set values thereof are interpolated, whereby a proper hardware set value at any height position can be easily obtained.

When the scanning position of the specimen to which the laser light is irradiated is changed, the stored absolute height of the predetermined reference depth is varied in accordance with the undulation of the surface of the specimen. That is, even when the focus position is disposed at the same absolute height, the thickness of the specimen is varied before and after the scanning position is changed, so that proper observation could not be performed if the same hardware set value is used. According to the first aspect of the present invention, the height of each focus position is stored by using the relative height to the absolute value of the reference depth in the hardware setting storage unit, and thus by merely changing the absolute height of the reference depth, proper fluorescence observation can be performed at all the focus positions.

A second aspect of the present invention is a scanning optical device including a laser light source for emitting laser light, a scanning unit for scanning the surface of a specimen with the laser light emitted from the laser light source, a focus depth adjusting unit for adjusting the depth of a focus position in the specimen of the laser light scanned by the scanning unit, a fluorescence detector for detecting fluorescence generated from the focus position of the laser light in the specimen, a reference depth information storage unit for storing an absolute height of a predetermined reference depth of the focus position adjusted by the focus depth adjusting unit, a hardware setting storage unit for storing an absolute height at each focus position of the laser light and a hardware set value containing a set value of at least one of the laser light source, the scanning unit, and the fluorescence detector in association with each other, and a height information conversion unit for calculating the difference in the absolute height of the reference depth before and after the absolute height of the reference depth is changed when the absolute height of the reference depth is changed, and adding the difference to the absolute height at each focus position stored in the hardware setting storage unit.

According to the second aspect of the present invention, the laser light emitted from the laser light source is scanned on the surface of the specimen by operating the scanning unit, and focused to a deep position in the specimen which is adjusted by operating the focus depth adjusting unit, whereby fluorescence is generated in the specimen. The fluorescence generated in the specimen is detected by the fluorescence detector. A fluorescence image can be obtained on the basis of the scanning position of the scanning unit and the intensity information of fluorescence detected by the fluorescence detector.

In this case, when fluorescence images are obtained while varying the depth of the focus position of the laser light at the same scanning position, the focus depth adjusting unit is operated on the basis of the absolute height at each focus position stored in the hardware setting storage unit, and hardware such as the laser light source, the scanning unit or the fluorescence detector can be set in the hardware set value stored in the hardware setting storage unit in association with the relative height on a focus-position basis.

As a result, the setting of the hardware can be implemented every focus position in consideration of the effect such as scattering or the like due to the thickness of the specimen, and proper fluorescence observation can be performed at all the focus positions. The predetermined reference depth may be set to the surface position of the specimen, for example. When the absolute height stored in the hardware setting storage unit is not continuous, a plurality of stored absolute heights and the hardware set values thereof are interpolated, whereby a proper hardware set value at any height position can be easily obtained.

Furthermore, when the scanning position of the laser light is changed, the stored absolute height of the predetermined reference depth is varied due to undulation of the surface of the specimen. That is, even when the focus position is set to the same absolute height before and after the scanning position is changed, proper observation cannot be performed if the same hardware set value is used because the thickness of the specimen varies. According to the second aspect of the present invention, when the absolute height of the reference depth is changed, by operating the height information conversion unit, the difference in the absolute height of the reference depth before and after the absolute height of the reference depth is changed is calculated, and the thus-calculated difference is added to the absolute height of each focus position, whereby proper fluorescence observation can be performed at all the focus positions by merely changing the absolute height of the reference depth.

In the first and second aspects, the laser light source may be a multiphoton excitation laser light source for emitting ultrashort pulse laser light. In this case, fluorescence generated only at each focus position can be easily detected and a clear fluorescence image can be obtained.

Furthermore, in the first and second aspects, the hardware set value may be set to a set value to obtain a fluorescence set value having predetermined brightness at each focus position of the laser light.

In this case, the fluorescence image having the predetermined brightness can be obtained at all the focus positions, and proper observation can be performed with no occurrence of uneven brightness in the depth direction.

In the first and second aspects, the scanning optical device may be further equipped with a reference depth detector for detecting the predetermined reference depth of the focus position of the laser light in the specimen, and the reference depth information storage unit may store the absolute height of the reference depth detected by the reference depth detector.

In this case, by operating the reference depth detector, the absolute height of the reference depth can be more accurately grasped, and proper hardware setting can be applied at each focus position, so that proper observation can be performed.

In the scanning optical device according to the first and second aspects, the reference depth information storage unit stores the absolute height at the reference depth and the hardware set value in association with each other, and a set value correcting unit for correcting the hardware set value at each focus position on the basis of a variation amount of the set value when the set value at the reference depth varies may be provided.

In this case, even when the hardware set value applied to the observation of the reference depth is varied because the absolute height of the reference depth is changed, the hardware set value at each focus position is corrected on the basis of the variation amount of the set value applied to the observation of the reference depth by operating the set value correcting unit, the proper observation can be performed. For example, in a case where the surface of the specimen is set to the reference depth, if the surface of the specimen is covered with water, another scattering medium, or the like, a hardware set value for obtaining the same level fluorescence image at the reference depth is varied due to variation of the thickness of the scattering medium. According to this invention, in such a case, a proper hardware set value can be applied to each focus position, and thus proper observation can be performed.

A third aspect of the present invention is an observation method for scanning a laser light focused to a specimen in a direction intersecting to a depth direction of the specimen while changing a focus position in the depth direction, thereby obtaining a two-dimensional fluorescence image at each depth position, including: storing an absolute height of a predetermined reference depth of the focus position of the laser light in the specimen; storing a relative height to the absolute height of the reference depth at each focus position of the laser light and a hardware set value containing laser light intensity, scanning speed, and fluorescence detection sensitivity at the focus position in association with each other; applying the stored relative height to the absolute height of the reference depth after the absolute height of the reference depth is changed when the absolute height of the reference depth is changed; and obtaining a fluorescence image by using the hardware set value stored in association with the relative height.

A fourth aspect of the present invention is an observation method for scanning a laser light focused to a specimen in a direction intersecting to a depth direction of the specimen while changing a focus position in the depth direction, thereby obtaining a two-dimensional fluorescence image at each depth position, including: storing an absolute height of a predetermined reference depth of the focus position of the laser light in the specimen; storing the absolute height at each focus position of the laser light and a hardware set value containing laser light intensity, scanning speed and fluorescence detection sensitivity at the focus position in association with each other; calculating the difference in the absolute height of the reference depth before and after the absolute height of the reference depth is changed when the absolute height of the reference depth is changed; correcting the absolute height by adding the difference to the stored absolute height to obtain an absolute height at a new focus position; and obtaining a fluorescence image by using the corrected absolute height at the focus position and the corresponding hardware set value.

A fifth aspect of the present invention is an observation method for scanning a laser light focused to a specimen in a direction intersecting to a depth direction of the specimen while changing a focus position in the depth direction, thereby obtaining a two-dimensional fluorescence image at each depth position, including: storing an absolute height at a predetermined reference depth of the focus position of the laser light in the specimen and hardware set values containing laser light intensity, scanning speed, and fluorescence detection sensitivity at the reference depth in association with one another; storing a height at each focus position of the laser light and a hardware set value containing laser light intensity, scanning speed, and fluorescence detection degree at the focus position in association with each other; correcting the stored hardware set value at each focus position in accordance with a variation amount when each kind of set value at the reference depth is varied; and obtaining a fluorescence image by using each corrected kind of set value.

According to the present invention, there can be achieved an effect that a clear fluorescence image can be easily obtained irrespective of variation of scattering due to variation of the depth of a focus position in the specimen.

BRIEF DESCRIPTION OF THE SEVERAL VIEWS OF THE DRAWINGS

FIG. 10 is a flowchart showing the processing of a control unit of a scanning optical device shown in FIG. 9.

DETAILED DESCRIPTION OF THE INVENTION

A scanning optical device 1 according to an embodiment of the present invention will be described with reference to FIGS. 1 to 6.

Figure 1:
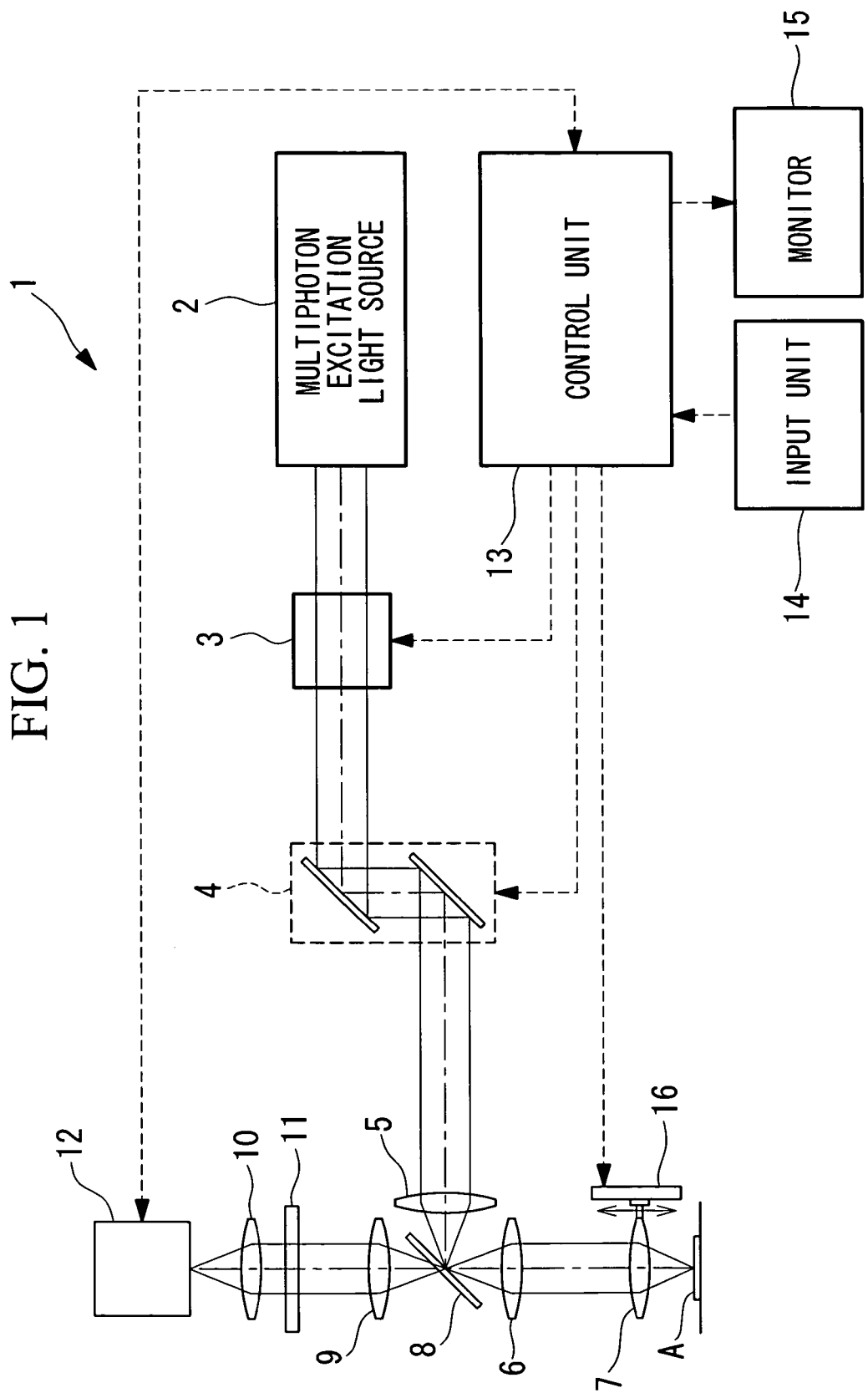
FIG. 1 is a diagram showing the overall construction of a scanning optical device according to a first embodiment of the present invention.

The scanning optical device 1 according to this embodiment is, for example, an optical device utilizing a multiphoton excitation phenomenon, and as shown in FIG. 1, the scanning optical device 1 includes a multiphoton excitation light source (laser light source) 2 for emitting ultrashort pulse laser light, a laser intensity adjusting unit 3 for adjusting the intensity of the ultrashort pulse laser light emitted from the multiphoton excitation light source 2, a scanner (scanning unit) 4 for two-dimensionally scanning the ultrashort pulse laser light, a pupil projection lens and an imaging lens 6 for focusing the scanned ultrashort pulse laser light, an objective lens 7 for focusing the ultrashort pulse laser light substantially-collimated by the imaging lens 6 to a specimen (sample) A and condensing fluorescence generated in the specimen A, a dichroic mirror 8 for separating the fluorescence which is collected by the objective lens 7 and returned through the imaging lens 6 from the ultrashort pulse laser light, collector lenses 9 and 10 for collecting the separated fluorescence, a barrier filter 11 for interrupting the ultrashort pulse laser light contained in the fluorescence, and a photodetector (fluorescence detector) 12 for detecting the fluorescence collected by the collector lenses 9, 10.

The scanning optical device 1 according to this embodiment includes a control unit 13 for controlling the laser intensity adjusting unit 3, the scanner 4, and the photodetector 12, an input unit 14 for inputting various kinds of information to the control unit 13 by an observer, and a monitor 15 for displaying a multiphoton fluorescence image constructed by the control unit 13. The objective lens 7 includes a focus position adjusting mechanism (focus depth adjusting unit) 16 for moving the objective lens 7 in the optical axis direction. The focus position adjusting mechanism 16 is controlled by the control unit 13.

The multiphoton excitation light source 2 emits ultrashort pulse laser light having predetermined intensity. The laser intensity adjusting unit 3 is constructed by an acousto-optic element, for example, and adjusts the intensity of the ultrashort pulse laser light incident to the scanner 4 on the basis of an instruction from the control unit 13.

Figure 2:
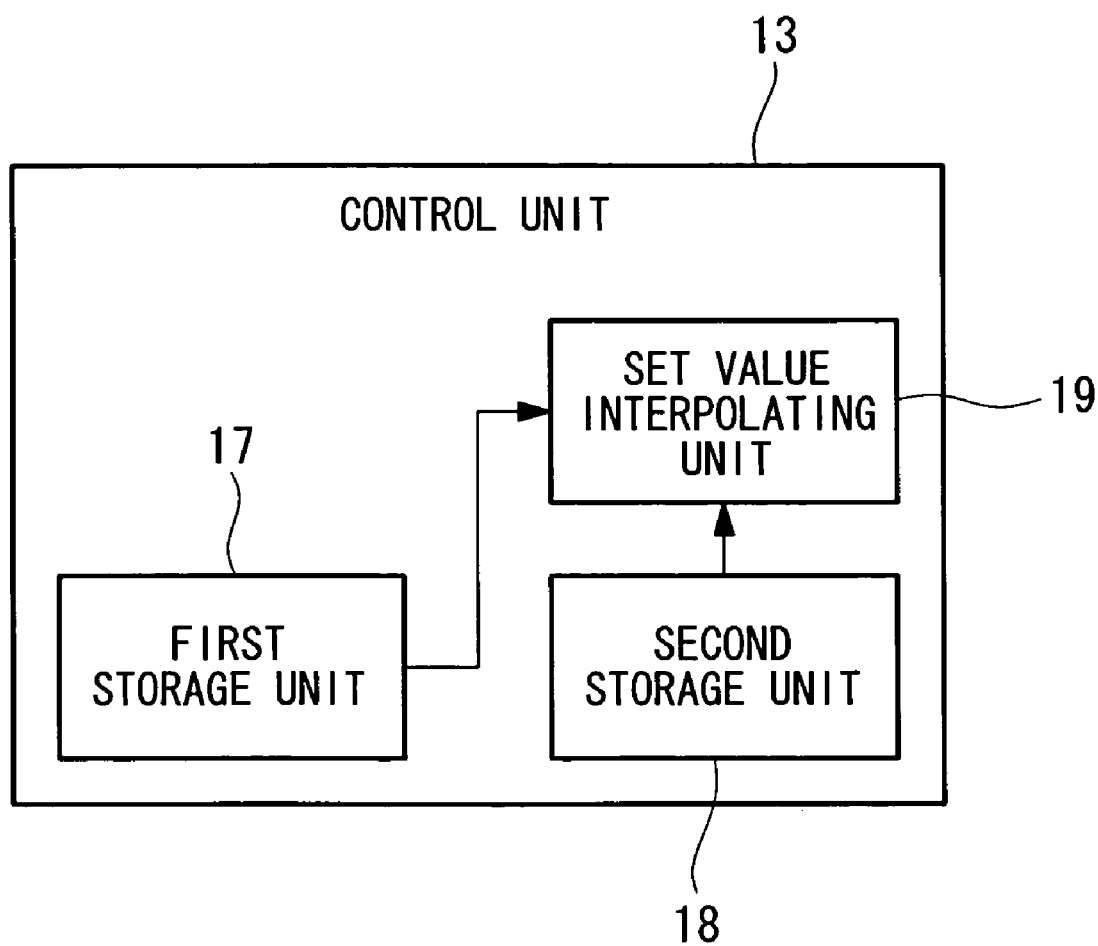
FIG. 2 is a block diagram showing a control unit of the scanning optical device of FIG. 1.
Figure 6:
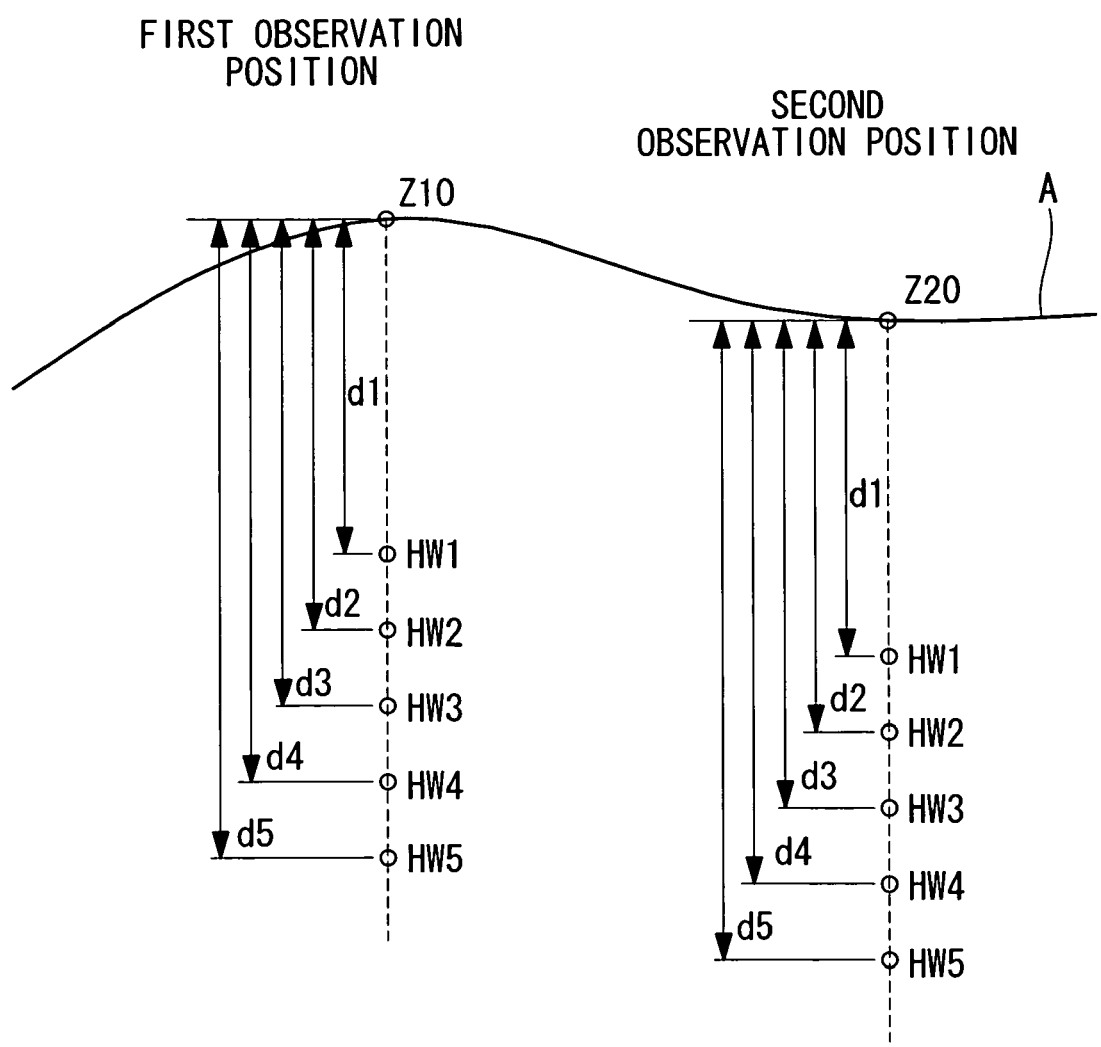
FIG. 6 is a diagram showing re-use of the hardware set value when different observation positions are observed by the scanning optical device of FIG. 1.

As shown in FIGS. 2 and 6, the control unit 13 includes a first storage unit (reference depth information storage unit) 17 for storing the absolute height Zo of the surface position (reference depth) of the specimen A at a predetermined observation position, and a second storage unit (hardware setting storage unit) 18 for storing the distance (relative height) $d_1$ to $d_5$ from the surface position to each of focus positions which are arranged in the depth direction of the specimen A at the observation position so as to be spaced from one another and at least one set value (hereinafter referred to as "hardware set value") $HW_1$ to $HW_5$ of the laser intensity adjusting unit 3, the scanner 4 and the photodetector 12 to obtain a fluorescence image having the same brightness condition at each focus position while the distances $d_1$ to $d_5$ are associated with the hardware set values $HW_1$ to $HW_5$. Here, the "absolute height" and the "relative height" are position coordinates with respect to the movement in the optical axial direction in the focus position adjusting mechanism 16.

The brightness of an image is adjusted by setting "the intensity of a laser light irradiated to the specimen", "the scanning speed per pixel" and "detection sensitivity" to the laser intensity adjusting unit 3, the scanner 4 and the photodetector 12 as hardware set values, respectively. These hardware set values may be arbitrarily combined with one another.

Furthermore, the control unit 13 includes a set value interpolating unit (height information conversion unit, set value correcting unit) 19 for interpolating the distances $d_1$ to $d_5$ and the hardware set values $HW_1$ to $HW_5$ stored in the second storage unit 18 to calculate a set value for obtaining a fluorescence image having the same brightness at any focus position between the stored focus positions. A linear interpolation method or any curved-line interpolating method may be adopted as the interpolating method in the set value interpolating unit 19.

An observation method using the thus configured scanning optical device 1 according to this embodiment will be described hereunder.

Figure 3:
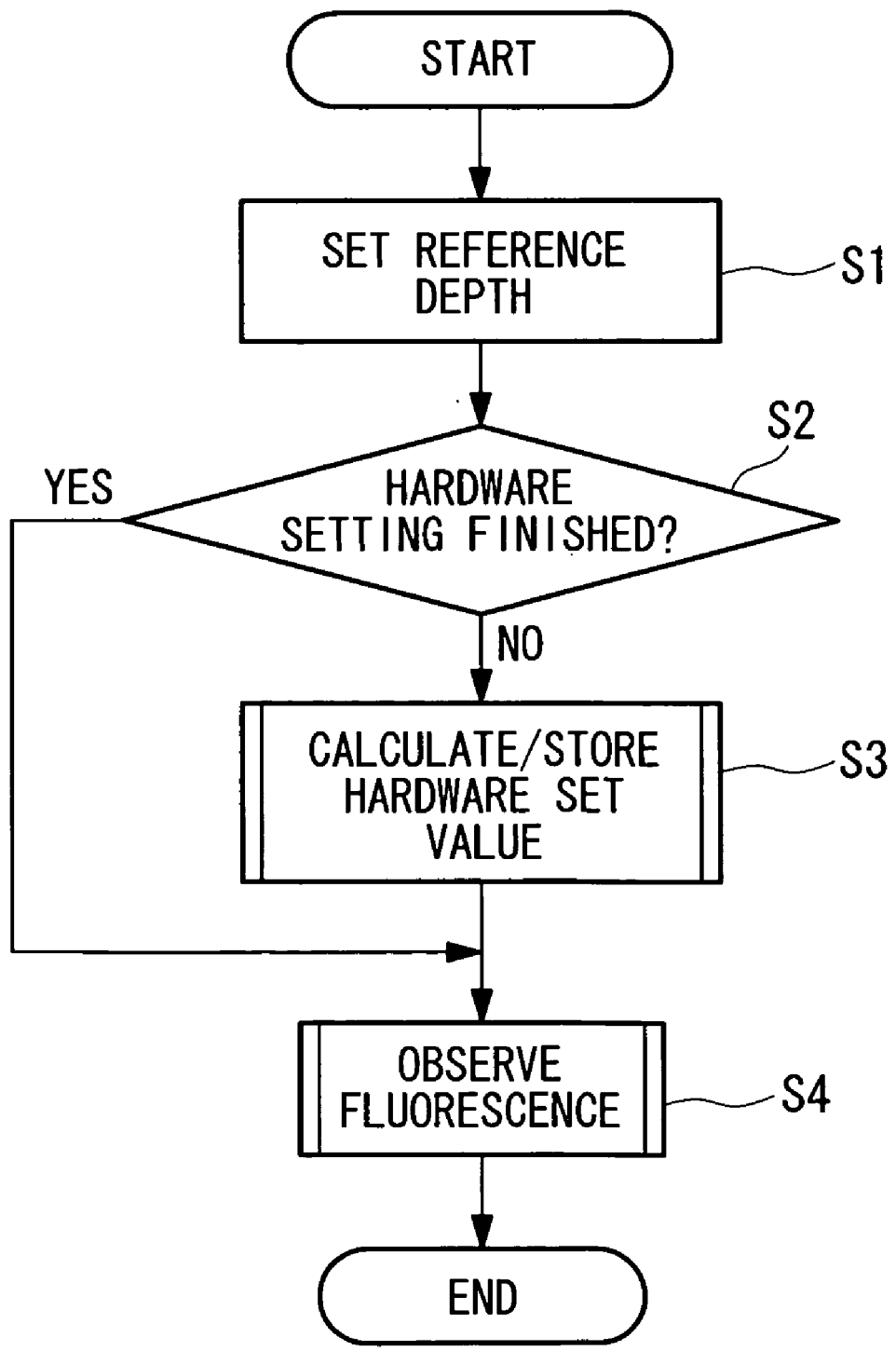
FIG. 3 is a flowchart showing the processing of the control unit of the scanning optical device of FIG. 1.

In order to obtain a plurality of fluorescence images in the depth direction of the specimen A by using the scanning optical device 1 according to this embodiment, the absolute height Zo of the surface position at a predetermined observation position is first stored in the first storage unit 17 (step S1) as shown in FIG. 3. An observer may manually store the absolute height Zo of the surface position from the input unit 14 into the first storage unit 17 while viewing the monitor 15. Alternatively, it may be adopted to obtain an image while the objective lens 7 is moved over a predetermined range by the focus position adjusting mechanism 16, judge a position providing the highest contrast in the image as a surface position and store the absolute height Zo of the position into the first storage unit 17.

Subsequently, it is judged whether hardware setting has been already carried out (step S2), and if no setting has been carried out, the hardware setting is carried out (step S3). If the hardware setting has been carried out, a multiphoton fluorescence image of the specimen A over a desired depth range is obtained by using the hardware set values $HW_1$ to $HW_5$ stored in the second storage unit 18 (step S4).

Figure 4:
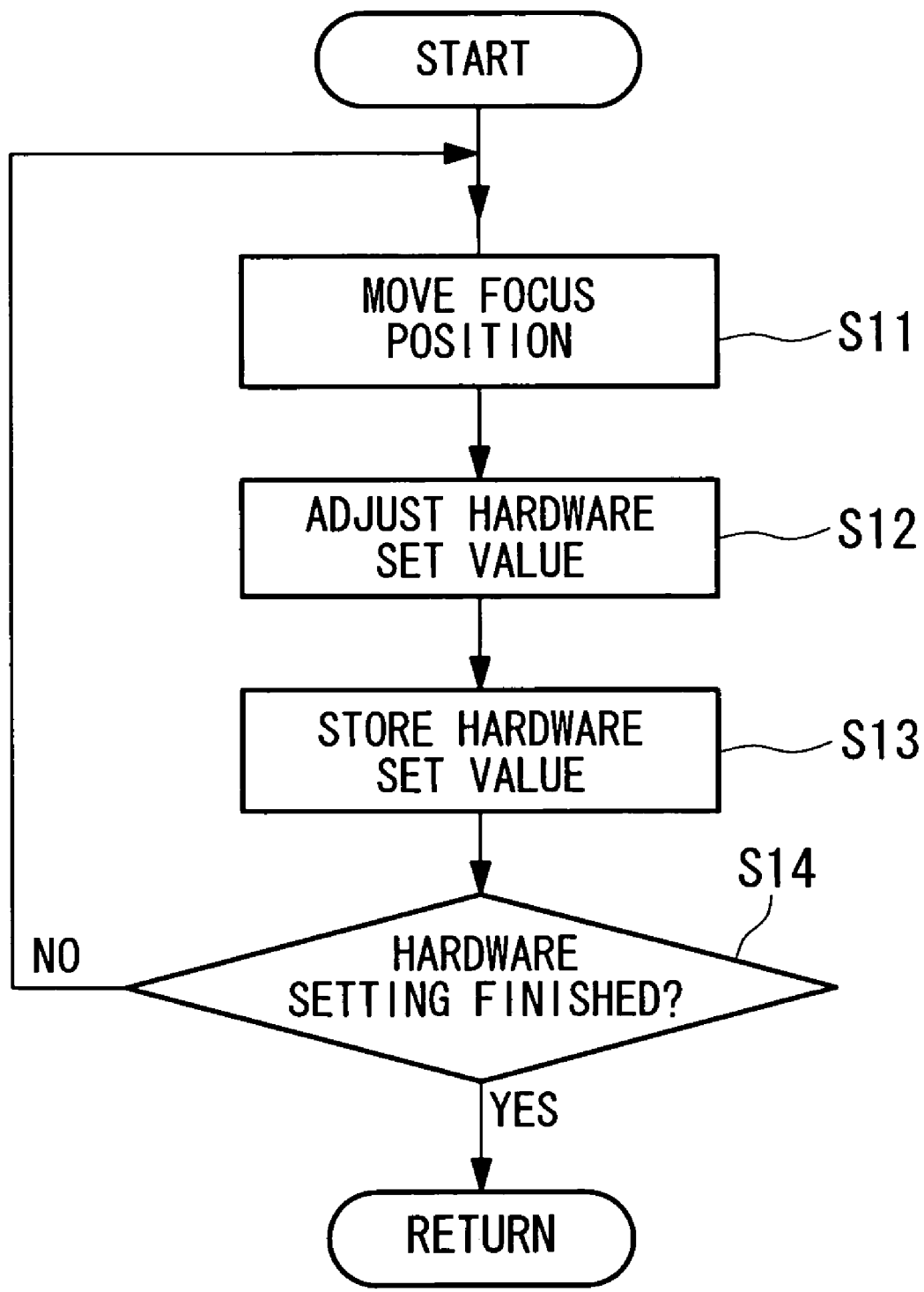
FIG. 4 is a flowchart showing the processing of setting a hardware set value in the processing of FIG. 3.

As shown in FIG. 4, the hardware setting is carried out at a plurality of places while the objective lens 7 is downwardly moved by operating the focus position adjusting mechanism 16 from the state that the focus position is disposed on the surface of the specimen A. Here, the downward movement of the objective lens 7 means that the objective lens 7 is moved so as to be close to the specimen A. Specifically, by operating the focus position adjusting mechanism 16, the objective lens 7 is downwardly moved (step S11), and the hardware set value is manually or automatically adjusted so as to attain the same brightness condition at each focus position (step S12), and the adjusted hardware set value is stored into the second storage unit 18 in association with the distances $d_1$ to $d_5$ from the surface position at each focus position (step S13). Then, it is judged whether the hardware setting is finished (step S14). If the hardware setting is not finished, the processing of steps S11 to S14 is repeated. The focus position of the laser light at which the hardware setting is carried out may be coincident with or different from a focus position at the next image obtaining step S4.

Figure 5:
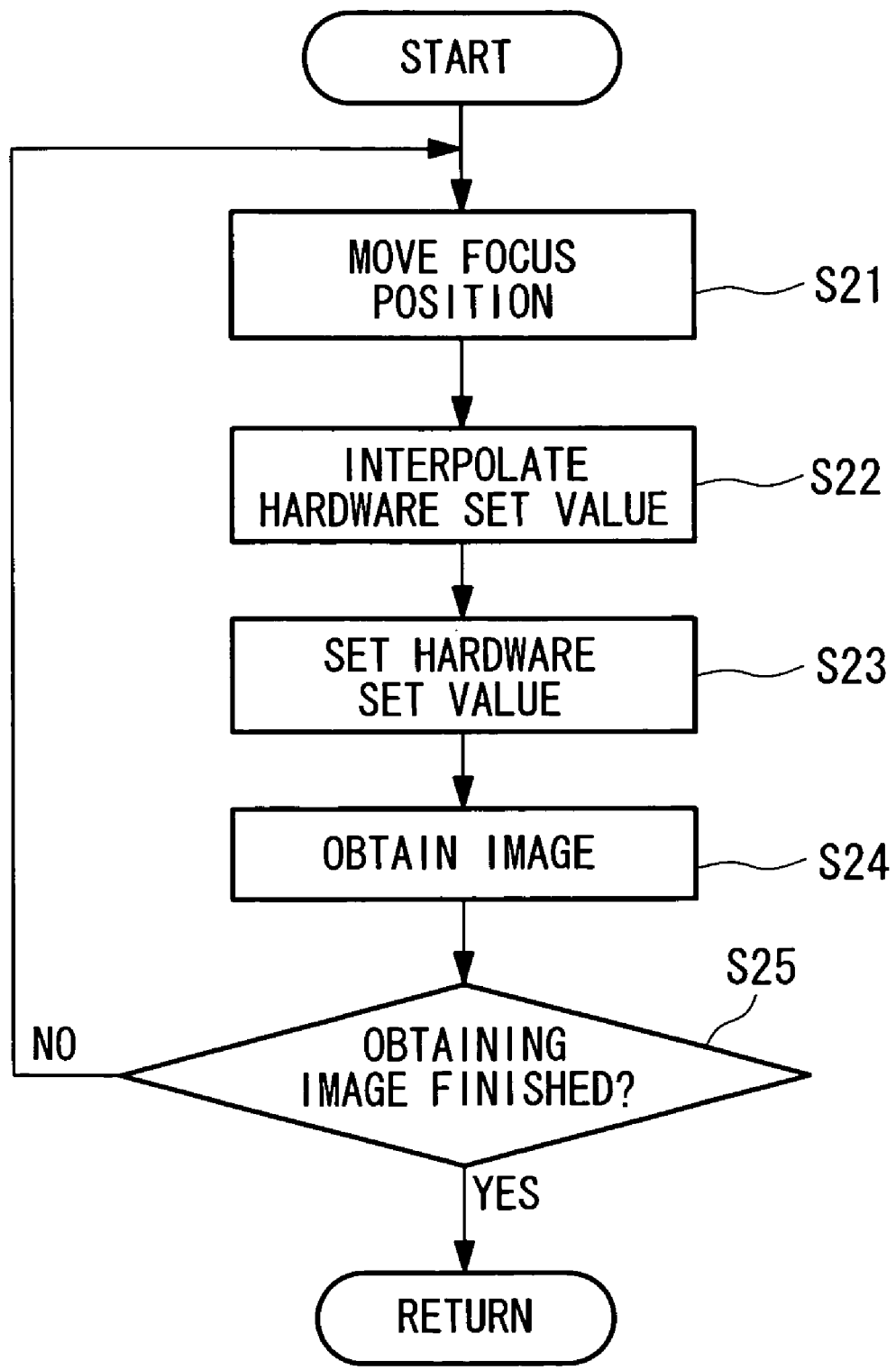
FIG. 5 is a flowchart showing the processing of fluorescence observation in the processing of FIG. 3.

In order to obtain the multiphoton fluorescence image, as shown in FIG. 5, by operating the focus position adjusting mechanism 16, the focus position of the laser light is moved to a predetermined depth position in an observation range which is input from the input unit by the observer (step S21), and hardware set values at that position are calculated and set by the set value interpolating unit 19 (step S22). By using the set hardware set values, the ultrashort pulse laser light is emitted from the multiphoton excitation light source 2, the ultrashort pulse laser light is two-dimensionally scanned by the scanner 4, and fluorescence is detected by the photodetector 12, thereby obtaining a two-dimensional multiphoton fluorescence image (step S23).

It is judged whether multiphoton fluorescence images at all the focus position in the observation range are obtained (step S24), and if this processing is not finished, the processing of steps S21 to S24 is repeated.

As described above, the multiphoton fluorescence images obtained at the respective focus positions can be obtained as multiphoton fluorescence images having the same brightness condition in spite of the difference in the scattering amount of the laser light among these multiphoton fluorescence images because the distances $d_1$ to $d_5$ from the surface position of the specimen A are different. Accordingly, unevenness in brightness can be prevented from occurring in the multiphoton fluorescence images obtained in the depth of the specimen A, and thus proper observation can be performed.

In this case, according to the scanning optical device 1 of this embodiment, the distances $d_1$ to $d_5$ from the surface position of the specimen A and the hardware set values $HW_1$ to $HW_5$ at the respective positions are stored in association with one another in the second storage unit 18. Therefore, even when the absolute height $Z_0$ of the surface position of the specimen A is varied by moving the observation range in the direction perpendicular to the optical axis, it is unnecessary to carrying out the hardware setting again.

That is, as shown in FIG. 6, by setting the absolute height $Z_{10}$ of the surface position of the specimen A, and the distances $d_1$ to $d_5$ from the surface position of the specimen A and the hardware set values $HW_1$ to $HW_5$ at a plurality of focus positions at the first observation position, even when the absolute height $Z_{20}$ of the surface position of the specimen A is varied from $Z_{10}$ to $Z_{20}$ through the movement from the first observation position to the second observation position different from the first position, the hardware set values $HW_1$ to $HW_5$ stored in the second storage unit 18 may be directly used as hardware set values $HW_1$ to $HW_5$ at positions which are spaced from the new surface position by the distances $d_1$ to $d_5$ and stored with respect to the absolute height $Z_{20}$ of the new surface position.

Accordingly, at an observation position different from an observation position at which hardware set values $HW_1$ to $HW_5$ are set, the set hardware set values $HW_1$ to $HW_5$ can be used again, and thus the time and labor required for the observation can be reduced.

In this embodiment, the hardware set values $HW_1$ to $HW_5$ are re-used when the observation position with respect to the same specimen A is changed, however, the present invention is not limited to this mode. The hardware set values $HW_1$ to $HW_5$ can be re-used for a completely different specimen A if the optical characteristic of the specimen is identical.

In this embodiment, the multiphoton excitation scanning optical device 1 using the multiphoton excitation phenomenon is described as an example. However, the present invention is not limited to this scanning optical device 1, and it may be applied to a confocal scanning optical device.

Figure 7:
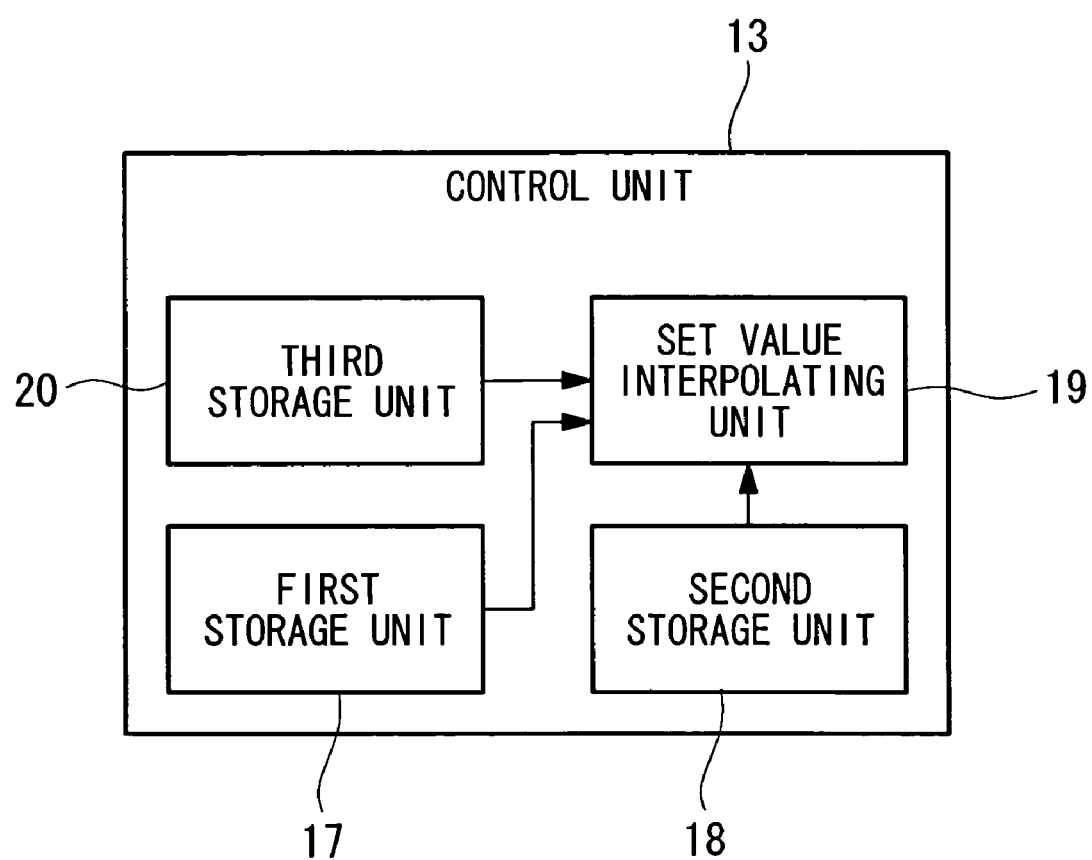
FIG. 7 is a block diagram showing a control unit of a scanning optical device according to a second embodiment of the present invention.

Next, a scanning optical device according to a second embodiment of the present invention will be described hereunder with reference to FIGS. 7 and 8.

In the following description of this embodiment, constituent elements of this embodiment which are common to the construction of the scanning optical device 1 according to the first embodiment described above are represented by the same reference numerals, and the description thereof is omitted.

Figure 8:
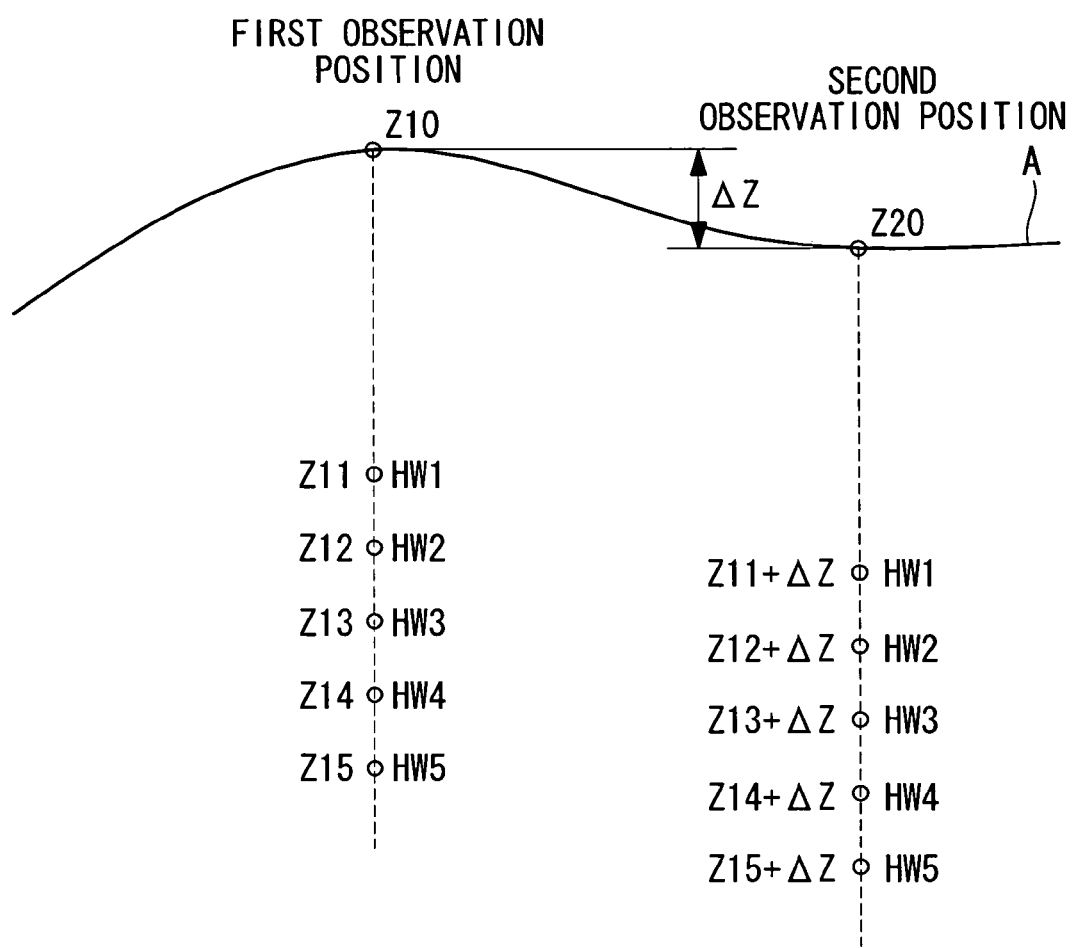
FIG. 8 is a diagram showing re-use of a hardware set value when different observation positions are observed in the scan optical device of FIG. 7.

As shown in FIG. 8, the scanning optical device 1 according to this embodiment is different from the scanning optical device 1 according to the first embodiment in that the data to be stored in the second storage unit 18 are the absolute heights $Z_{11}$ to $Z_{15}$ of the respective focus positions in place of the distances $d_1$ to $d_5$ from the surface positions of the plurality of focus positions which are arranged in the depth direction of the specimen A at the observation position so as to be spaced from one another, in that the control unit 13 is provided with a third storage unit 20 for storing the absolute height $Z_{20}$ at a new surface position, and in the operation of the set value interpolating unit 19.

The set value interpolating unit 19 calculates the difference $\Delta Z$ between the set absolute height $Z_{10}$ of the surface position stored in the first storage unit 17 and the absolute height $Z_{20}$ of the new surface position, and the difference $\Delta Z$ is added to the absolute heights $Z_{11}$ to $Z_{15}$ of the respective focus positions stored in the second storage unit 18 to calculate new absolute heights $Z_{11}+\Delta Z$ to $Z_{15}+\Delta Z$. Furthermore, the set value interpolating unit 19 sets the hardware set values $HW_1$ to $HW_5$ stored in the second storage unit 18 as hardware set values $HW_1$ to $HW_5$ to the new absolute heights $Z_{11}+\Delta Z$ to $Z_{15}+\Delta Z$, and the hardware set value of each focus position is interpolatively calculated on basis of these hardware set values.

According to the thus configured scanning optical device of this embodiment, as in the case of the scanning optical device 1 according to the first embodiment, the hardware set values $HW_1$ to $HW_5$ registered at one observation position can be re-used at a different observation position of the surface position, and the labor and time required for the observation can be reduced.

A scanning optical device according to a third embodiment of the present invention will be described with reference to FIGS. 9 and 10.

In the following description of this embodiment, constituent elements common to the construction of the scanning optical device 1 according to the first embodiment described above are represented by the same reference numerals, and the description thereof is omitted.

The scanning optical device according to this embodiment is different from the scanning optical device 1 according to the first embodiment in that the information stored in the first storage unit 17 contains not only the absolute height $Z_{10}$ of the surface position, but also the hardware set value $HW_{01}$ at the surface position, in that the control unit 13 is provided with a third storage unit 20 for storing the absolute height $Z_{20}$ of a new surface position and a hardware set value $HW_{02}$, and in the operation of the set value interpolating unit 19.

The set value interpolating unit 19 calculates the difference $\Delta HW$ between the hardware set value $HW_{01}$ at the surface position stored in the first storage unit 17 and the new hardware set value $HW_{02}$ at the surface position stored in the third storage unit 20, calculates new hardware set values $f(HW_1)$ to $f(HW_5)$ of respective focus positions by a conversion function $f(HW)$ for adding the difference $\Delta HW$ to the hardware set values $HW_1$ to $HW_5$ of the respective focus positions stored in the second storage unit 18 (step S5), and interpolatively calculates the hardware set value of each focus position on the basis of the above values.

According to the thus configured scanning optical device of this embodiment, as in the case of the scanning optical device 1 of the first embodiment, the hardware set values $HW_1$ to $HW_5$ registered at one observation position can be re-used at a different observation position of the surface position, and the labor and time required for the observation can be reduced.

Figure 9:
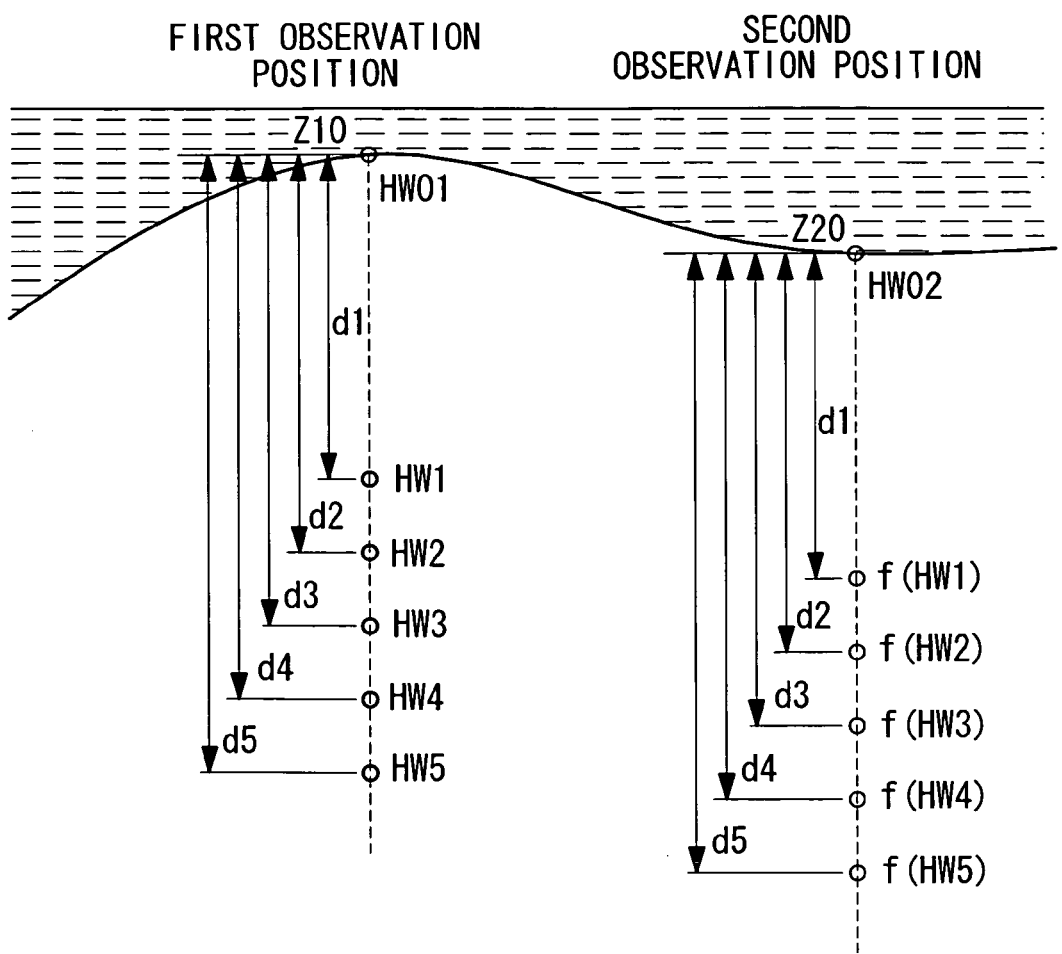
FIG. 9 is a diagram showing re-use of a hardware set value when different observation positions are observed in a scanning optical device according to a third embodiment of the present invention.

Furthermore, according to the scanning optical device of this embodiment, as shown in FIG. 9, even when the surface of the specimen A is covered with water or other scattering medium M and the thickness of the scattering medium is varied every observation position due to undulation of the surface of the specimen A or the like, the hardware set values $f(HW_1)$ to $f(HW_5)$ at the respective focus positions in the specimen A can be properly set in consideration of the above scattering, so that proper observation can be performed with no unevenness of brightness.

In this embodiment, the difference $\Delta HW$ between the hardware set values $HW_{01}$ and $HW_{02}$ at the surface position of the two observation positions is added as the conversion function $f(HW)$. However, in place of this conversion function $f(HW)$, any other conversion function may be adopted.

It is preferable to prepare as the conversion function a conversion function which is different every channel of the photodetector 12 or every unit of the multiphoton excitation light source 2.

Furthermore, the content of the third embodiment may be used in combination with the control method using the absolute position as in the case of the second embodiment.

What is claimed is:

1. A scanning optical device comprising:
   a laser light source for emitting laser light;
   a scanning unit for scanning a surface of a specimen with the laser light emitted from the laser light source;
   a focus depth adjusting unit for adjusting a depth of a focus position in the specimen of the laser light scanned by the scanning unit;
   a fluorescence detector for detecting fluorescence generated from the focus position of the laser light in the specimen;
   a reference depth information storage unit for storing an absolute height of a predetermined reference depth of the focus position adjusted by the focus depth adjusting unit;
   a hardware setting storage unit for storing (i) a relative height with respect to the absolute height of the reference depth, at each depth of a plurality of the focus positions at different depths adjusted by the focus depth adjusting unit, and (ii) a hardware set value in association with each said relative height, wherein each hardware set value contains a set value of at least one of the laser light source and the fluorescence detector; and
   a control unit for obtaining a plurality of fluorescence information in a depth direction of the specimen by detecting fluorescence from the specimen by the fluorescence detector after varying the depth of the focus position of the laser light with respect to the reference depth by using the focus depth adjusting unit and carrying out setting of at least one of the laser light source and the fluorescence detector in association with the depth of the focus position based on the stored hardware set values.

2. The scanning optical device according to claim 1, wherein the laser light source is a multiphoton excitation laser light source which emits ultrashort pulse laser light.

3. The scanning optical device according to claim 1, wherein the hardware set value is a set value to obtain a fluorescence image having predetermined brightness at each focus position of the laser light.

4. The scanning optical device according to claim 1, further comprising:

a reference depth detector for detecting the predetermined reference depth of the focus position of the laser light in the specimen, wherein the reference depth information storage unit stores the absolute height of the reference depth detected by the reference depth detector.

5. The scanning optical device according to claim 1, wherein:

the reference depth information storage unit stores the absolute height at the reference depth and a further hardware set value in association with each other, and the scanning optical device further comprises a set value correcting unit for correcting the hardware set value at each depth stored in the hardware setting storage unit based on a variation amount of the hardware set value when the hardware set value at the reference depth varies.

6. The scanning optical device according to claim 1, wherein the control unit applies the stored relative heights to the absolute height of the reference depth after the absolute height of the reference depth is changed when the absolute height of the reference depth is changed, and obtains a fluorescence image at each of a plurality of depths by using the hardware set values stored in association with the relative heights.

7. A scanning optical device comprising:

a laser light source for emitting laser light;

a scanning unit for scanning a surface of a specimen with the laser light emitted from the laser light source;

a focus depth adjusting unit for adjusting a depth of a focus position in the specimen of the laser light scanned by the scanning unit;

a fluorescence detector for detecting fluorescence generated from the focus position of the laser light in the specimen;

a reference depth information storage unit for storing an absolute height of a predetermined reference depth of the focus position adjusted by the focus depth adjusting unit;

a hardware setting storage unit for storing (i) an absolute height at each depth of a plurality of the focus positions at different depths adjusted by the focus depth adjusting unit and (ii) a hardware set value in association with each said absolute height, wherein each hardware set value contains containing a set value of at least one of the laser light source and the fluorescence detector in association with each other;

a height information conversion unit for calculating difference in absolute height of the reference depth before and after the absolute height of the reference depth is changed when the absolute height of the reference depth is changed, and adding the difference to the absolute height at each depth stored in the hardware setting storage unit; and a control unit for obtaining a plurality of fluorescence information in a depth direction of the specimen by detecting fluorescence from the specimen by the fluorescence detector after varying the depth of the focus position of the laser light with respect to the reference depth by using the focus depth adjusting unit and carrying out setting of at least one of the laser light source and the fluorescence detector in association with the depth of the focus position based on the stored hardware set values.

8. The scanning optical device according to claim 7, wherein the laser light source is a multiphoton excitation laser light source which emits ultrashort pulse laser light.

9. The scanning optical device according to claim 7, wherein the hardware set value is a set value to obtain a fluorescence image having predetermined brightness at each focus position of the laser light.

10. The scanning optical device according to claim 7, further comprising:

a reference depth detector for detecting the predetermined reference depth of the focus position of the laser light in the specimen, wherein the reference depth information storage unit stores the absolute height of the reference depth detected by the reference depth detector.

11. The scanning optical device according to claim 7, wherein:

the reference depth information storage unit stores the absolute height at the reference depth and a further hardware set value in association with each other, and the scanning optical device further comprises a set value correcting unit for correcting the hardware set value at each depth stored in the hardware setting storage unit based on a variation amount of the hardware set value when the hardware set value at the reference depth varies.

* * * * *